United States Patent [19]

Blanch et al.

[11] Patent Number: 4,925,790

[45] Date of Patent: May 15, 1990

[54] METHOD OF PRODUCING PRODUCTS BY ENZYME-CATALYZED REACTIONS IN SUPERCRITICAL FLUIDS

[75] Inventors: Harvey W. Blanch, San Francisco; Theodore Randolph, Berkeley; Charles R. Wilke, El Cerrito, all of Calif.

[73] Assignee: The Regents of the University of California, Berkeley, Calif.

[21] Appl. No.: 771,366

[22] Filed: Aug. 30, 1985

[51] Int. Cl.$^5$ .................. C12P 33/00; C12P 13/00
[52] U.S. Cl. ........................... 435/52; 435/41; 435/128; 435/801; 435/813
[58] Field of Search ............ 435/11, 52, 55, 128, 435/156, 21, 41, 801, 813

[56] References Cited

U.S. PATENT DOCUMENTS 3,969,196  7/1976  Zosell .................................. 203/49

OTHER PUBLICATIONS

Butler, *Enzyme Microb. Tech.*, 1, (1979), pp. 253–259.
Zaks et al., *Science*, vol. 224, No. 4654, (1984), pp. 1249–1251.
Randolph et al., *Biotechnology Letters*, vol. 7, No. 5, pp. 325–328 (1985), (May 1985).
Hammond et al., *Applied Biochem. Biotechnol.*, 11(5), pp. 393–400, (1985).

*Primary Examiner*—Charles F. Warren
*Attorney, Agent, or Firm*—Flehr, Hohbach, Test, Albritton & Herbert

[57] ABSTRACT

A method is provided for producing a product by enzyme-catalyzed reaction using supercritical fluid as a solvent. Improved reaction times, conversion efficiencies and/or other efficiencies (such as improved ease of product recovery) are obtained.

9 Claims, 1 Drawing Sheet

METHOD OF PRODUCING PRODUCTS BY ENZYME-CATALYZED REACTIONS IN SUPERCRITICAL FLUIDS

The present invention is directed to a method of producing products by enzyme-catalyzed reactions. In particular, the present invention is directed to a method of producing products by enzyme-catalyzed reactions in supercritical fluids.

BACKGROUND OF THE INVENTION

Supercritical fluids are those fluids which exist as fluids at a temperature and pressure above the fluid critical temperature, $T_c$, and fluid critical pressure, $P_c$, respectively. As used herein, the term supercritical fluid may be either a pure fluid or a mixture of two or more fluids. The fluid critical temperature, $T_c$, and the fluid critical pressure, $P_c$, for most substances, including common liquids, are known and are defined, respectively, as that temperature and pressure above which a liquid and its vapor cannot coexist in equilibrium. However, in a system maintained in such that both the system pressure and temperature are higher than the critical temperature and pressure of the compound or mixture of compounds contained in the system, the system is said to contain a fluid under supercritical conditions. Supercritical fluids exhibit a number of advantageous properties when compared with conventional liquids, in particular, supercritical fluids may have improved properties as solvents. For example, the diffusivity of many substances may be greatly enhanced in a supercritical fluid as opposed to a conventional liquid of comparable density. The viscosity of a supercritical fluid may also be much lower than a conventional liquid solvent of comparable density. These two properties may make a supercritical fluid advantageous in facilitating mass-transfer operations. Another property of a supercritical fluid may be its sensitivity to the solubility of a particular compound therein to small changes in temperature and pressure. As an example, the solubility of naphthalene in supercritical carbon dioxide may change by a hundred-fold by small changes in temperature and pressure of the supercritical fluid. This sensitivity of solubility to small changes in temperature and pressure of a supercritical fluid has been used to effect separation of products by their solubilities. See, for example, U.S. Pat. No. 3,969,196. Separation schemes based on changes of solubility by small temperature and pressure perturbations of supercritical fluids have been used for extraction of caffeine from coffee beans (C. H. Kurzals, "Caffeine Extraction," presented at the Soc. Chem. Ind. Food Eng. Panel Symposium, CO2 in Solvent Extraction, London, (1982)), and for extraction of hops for beer production (See D. S. J. Gardner, "Industrial Scale Hops Extraction," presented at the Soc. Chem. Ind. Food Eng. Panel Symposium, CO2 in Solvent Extraction, London (1982)).

Another feature of supercritical fluids is that by selecting a supercritical solvent with a proper $T_c$, an extraction process may be conducted at relatively low temperatures, thus avoiding potential denaturation or decomposition of heat-liable compounds. Low temperature supercritical fluid processing has been utilized for extraction processes. However, application to other processes has been thus far reported only in the case of the hydrolysis of a biomass using supercritical water. See Vick Roy, J. R., and Converse, A. D., "Biomass Hydrolysis With Sulfur Dioxide and Water in the Region of the Critical Point", presented at the 1984 AICHE Annual Meeting, San Francisco, November 1984.

With respect to enzyme-catalyzed reactions in nonaqueous solvents, there has been work reported by Zaks, A., and Klibanov, A. M., *Science* 224 1249-1251 (1984), and Butler, L. G., *Enzyme Microb. Technol.* 1, 253-259 (1979). However, this work involves use of conventional liquid solvents.

SUMMARY OF THE INVENTION

The present invention provides a method for producing a product by enzyme-catalyzed reaction by contacting the substrate and enzyme in the presence of a supercritical fluid, i.e., a fluid under supercritical conditions of temperature and pressure. Under supercritical conditions of the fluid, the substrate is substantially more soluble, thereby improving the rate and/or efficiency of the enzyme catalyzed reaction. Furthermore, by using a supercritical fluid, the reaction may be conducted at a temperature sufficiently low to avoid denaturation or decomposition of the enzymes. The method according to the present invention further allows for removal of the products of the enzyme catalyzed reaction by changing the conditions of temperature and/or pressure of the supercritical fluid to effect precipitation of the products.

In the accompanying features:

DESCRIPTION OF THE INVENTION

Figure 1:
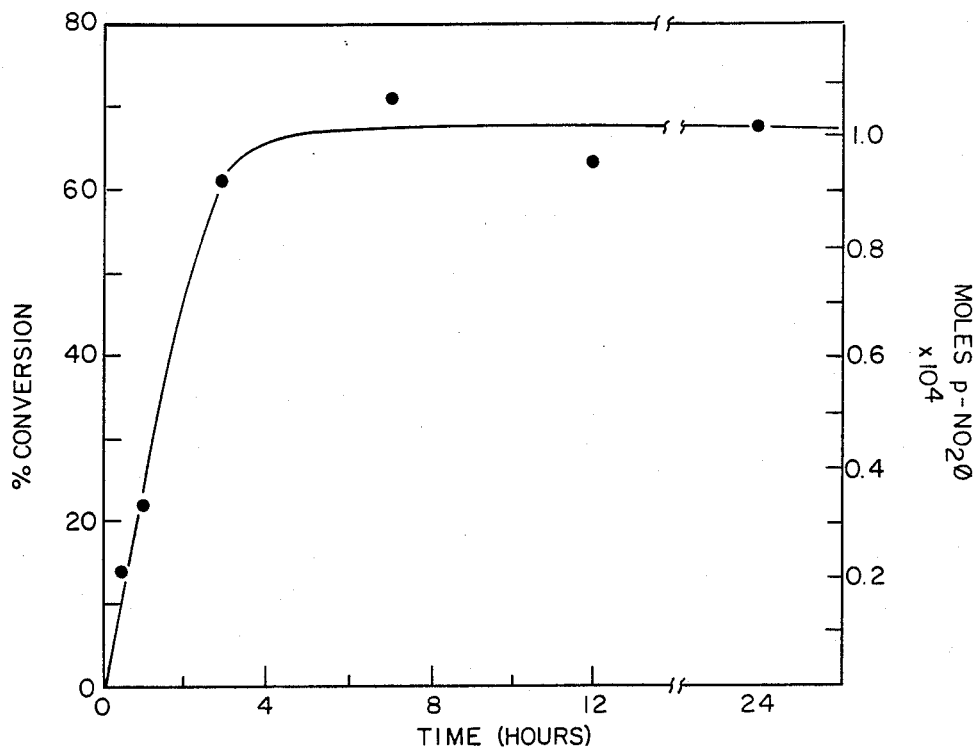
FIG. 1 is a plot of time versus percent conversion of the substrate for a batch reaction conducted according to the present invention under conditions shown in Example 1.

The present invention provides a method for producing a product by enzyme-catalyzed reaction by contacting the substrate and enzyme in the presence of a supercritical fluid. Under supercritical conditions of the fluid, the substrate is substantially more soluble than in aqueous solutions or organic aqueous liquid mixtures, thereby improving the rate and/or efficiency of the enzyme-catalyzed reaction. Furthermore the reaction may be conducted at a temperature sufficiently low to avoid denaturation or decomposition of the enzymes.

In the usual case, water will be present in the reaction mixture since it is normally a reactant in an enzyme-catalyzed reaction. However, in an alternative embodiment of the present invention, the initial concentration of water in the reaction mixture may be controlled such that it is low enough to drive the enzyme-catalyzed reaction in a reverse manner, i.e., to cause the reverse reaction to occur by the law of mass action to produce water and a dehydration product.

The fluids under supercritical conditions which may be utilized according to the present invention include, but are not limited to, carbon dioxide, oxygen, nitrous oxide, ethane, ethylene, and trifluoromethane. In addition, mixtures of these and other substances may be used as supercritical fluids. In particular, mixtures containing entrainers, including but not limited to methanol or acetone, may be used in supercritical fluid processing. Such entrainers may increase the solubility of the substrate to be used. As an example, the addition of less than 10 mole percent methanol in supercritical carbon dioxide greatly increases the solubility of cholesterol. The supercritical fluid to be utilized in each case may be selected in accordance with the solubility of the substrate to be used. The method according to the present invention is particularly useful where the reactants of enzyme-catalyzed reactions are only sparingly soluble or insoluble at normal temperatures and pressures in aqueous solutions, but are substantially soluble in a particular supercritical fluid. The enhanced solubility, usually accompanied by improved diffusivity, of the reactants and products of the enzyme-catalyzed reaction in the supercritical fluid provides an improved method for conducting enzyme-catalyzed reactions compared to those reactions conducted in conventional aqueous and/or organic solvent mixtures.

A particularly preferred supercritical fluid is carbon dioxide since it has been found that this does not denature most enzymes and permits enzyme activity to be maintained for a sufficient period of time to conduct the catalyzed reaction.

The enzymes which may be utilized in the method according to the present invention include any enzyme. Enzymes include those which would result in the production of useful pharmaceutical products, particularly those products or substrates which are insoluble or only sparingly soluble at normal temperatures and pressures in aqueous solutions, such as steroids.

The enzymes which are used in accordance with the present invention may be used in free solution in the supercritical fluid, or may be immobilized on a solid support such as on glass beads, polymeric beads, hollow fibers, or other means of immobilizing catalytic materials.

The enzymes in the supercritical solvent may also be used with a surfactant to form a reverse micelle around the enzyme and a small amount of water. The stabilizing effects of such "microemulsions" on enzyme activity are known in non-supercritical liquid mixtures of water, surfactants, and non-aqueous solvent. Enzymatic activity in reverse micelle systems in non-supercritical organic solvents is known for such diverse enzymes as chymotrypsin, trypsin, lysozyme, ribonuclease, pyrophosphatase, lactate dehydrogenase, alkaline phosphatase, pyruvate kinase, cytochrome c, hydrogenase, and 20-Beta hydroxysteroid dehydrogenase. An advantage of a reverse micelle is that while its high surface area (usually on the order of 100 $m^2/ml$) combined with high diffusivity of substrates in a supercritical solvent system may lead to elevated rates of reaction, the enzyme is protected from denaturation in the "pseudo-cellular" reverse micelle interior. Micelles may also be used to entrap a second enzyme used to regenerate cofactors, such as NAD+, which may be required in the reaction. The cofactor and enzyme required to regenerate it are thus protected from the environment, and are maintained in close proximity to the site of the reaction.

Figure 2:
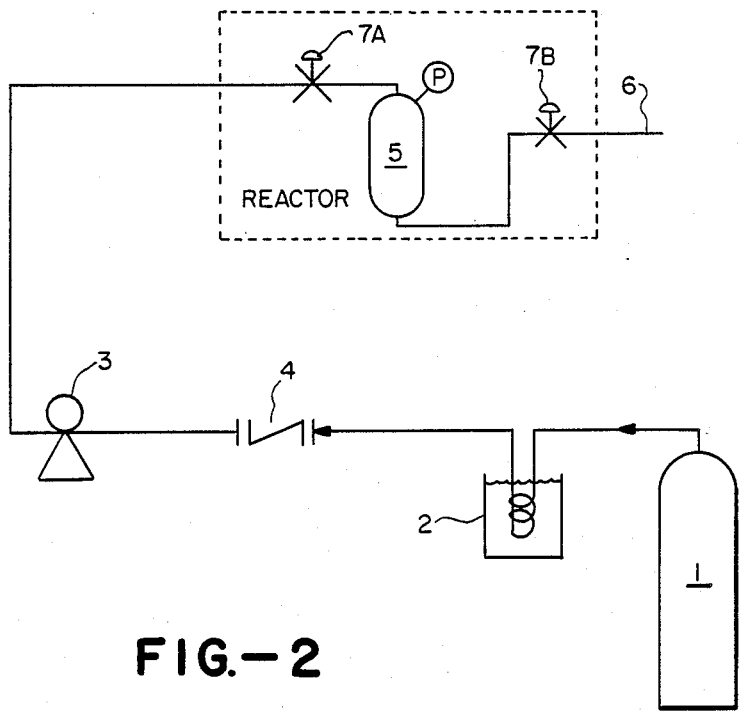
FIG. 2 illustrates a schematic apparatus for conducting the method of the present invention under batch conditions.

The enzyme-catalyzed reaction according to the present invention may be conducted by batch or continuous operation. An exemplary reactor for a batch operation is shown in FIG. 2. The dried material to be used as the solvent (eventually to be the supercritical fluid) may be maintained in storage tank 1 under ambient conditions as a gas or liquid. The material may then be withdrawn as needed and cooled in a precooling means 2, such as in an ice-salt bath. Pressure may then be increased by a high pressure pump means 3 after passing the cooled fluid through a checkvalve 4. After exiting the high pressure pump, the fluid will be ready for addition to the reactor. In the reactor 5, the enzyme will usually be added first through line 6 as free enzyme or as an enzyme immobilized in a conventional fashion. Valve means 7A and 7B appropriately control access to the reactor 5. The substrate may be added through line 6. The supercritical fluid may then be added by opening valve 7 and pumping into the reactor, preferably at a constant temperature, until the desired pressure within the reactor 5 is reached. The reactor will then be sealed off by closing all of the valves and the contents will be allowed to react for an appropriate length of time. The product and unreacted substrate, if any, may be recovered by cooling the reactor until the compounds precipitate from the solution or by reducing the pressure, which also may cause precipitation.

It will be recognized that other reactor configurations may be utilized, such as packed beds composed of enzymes immobilized on glass or polymer beads, fluidised beds, membrane reactors, and the like, which allow for continuous as well as batch operation.

In the usual case there will be water in the reactor, either added separately or with the enzyme and/or substrate, for the reason that many enzyme-catalyzed reactions consume water as a reactant. In one embodiment of the present invention, the equilibrium of the enzyme-catalyzed reaction may be perturbed, thereby reversing the reaction by mass action, by reducing the initial concentration of water in the reactor sufficiently to cause the reaction to run in the reverse manner. i.e., to produce water and a dehydration product.

The following examples are presented by means of illustration, but are not intended to limit the invention in any way.

EXAMPLE 1

In a stainless steel reaction chamber of internal volume 200 ml were placed 40 mg disodium p-nitrophenyl phosphate. Next 0.2 ml deionized water were pipetted into the reactor vessel. 2.0 mg of the enzyme alkaline phosphatase, EC 3.1.3.1, were sealed inside a thin-walled glass tube of dimensions $0.5 \times 3$ cm and placed inside the reactor.

The reactor was then flushed with approximately 5 volumes of carbon dioxide to remove any air. At a constant temperature of 35° C., liquid carbon dioxide (dry) was pumped using a high pressure liquid chromatography pump into the reactor, after first passing the carbon dioxide over a molecular sieve to remove any trace water. When the pressure in the reactor reached 100 atmospheres, the reactor was sealed, then shaken to shatter the glass vial containing the enzyme, thus initiating the reaction.

After a measured length of time, the reaction was quenched by immersing the vessel in liquid nitrogen until the carbon dioxide inside solidified. The vessel was then opened, and 40 ml of 4N NaOH solution added. The vessel was then allowed to warm to room temperature, subliming away the carbon dioxide but leaving the enzyme, products, and any unreacted disodium p-nitrophenyl phosphate behind in the NaOH solution.

After diluting 1:3 with deionized water, the solution was analyzed for p-nitrophenol by light absorbance at 410 nm. Typical results for batch runs terminated after various lengths of time are shown in FIG. 1. Maximum conversion of disodium p-nitrophenyl phosphate to p-nitrophenol approached 70%.

As a control, the above procedure was followed, but the enzymes were omitted. No p-nitrophenol could be detected in the control sample.

EXAMPLE 2

In a stainless steel reactor were placed 50.0 mg cholesterol, together with 1 mg cholesterol oxidase isolated from Pseudomonas, EC 1.1.3.6. At a constant temperature of 35° C., the reactor vessel was filled to a pressure of 100 atmospheres with a 1:9 mixture of oxygen and carbon dioxide. The reactor was then sealed and the contents were allowed to react for 12 hours at 35° C.

After 12 hours, the reactor was immersed in liquid nitrogen until the carbon dioxide was frozen. The reactor was then opened, and the carbon dioxide sublimed by warming to room temperature. The reactor was then rinsed with 2×25 ml spectral grade methylene chloride, dissolving any products and unreacted cholesterol. The methylene chloride solution was collected and a 10 microliter sample injected onto a reverse phase C-18 high pressure liquid chromatography column. The mobile phase used was a 96:2:2 methanol: methylene chloride:water mixture. Products were detected by U. V. absorptance at 242 nm. Cholest-4-en-3-one was detected, along with two unidentified products As a control, the above procedure was followed, but no enzyme were added. In the control sample, neither the cholest-4-en-3-one nor the two unidentified products could be detected.

EXAMPLE 3

In a 200 ml pressure vessel were placed 0.0231 g cholesterol. 0.5 mg cholesterol oxidase from Streptomyces (approximately 10 units; one unit will oxidize 1.0 micromole cholesterol to choles-4en-3one per minute in aqueous solution at pH 7.5), and 1.0 ml 0.01 N $Na_2HPO_4$ buffered at pH 7.0.

The reactor vessel was flushed with oxygen, then filled to 120 psi at 25° C. Carbon dioxide was next pumped into the vessel until the pressure reached 1400 psi at 35° C.

The contents of the bomb were allowed to react at a constant temperature of 35° C. for 2 hours, at which time the reaction was terminated by immersing the vessel in liquid nitrogen until the carbon dioxide solidified and the vessel could be opened. The vessel was warmed to −5° C., allowing the carbon dioxide to sublime. The bomb was rinsed with 2×10 ml spectral grade dichloromethane, which was collected and analyzed for cholest-4-en-3-one by injecting a 5 microliter sample onto a RP-18 HPLC column using methanol as the mobile phase. Cholest-4-en-3-one was detected by U.V. absorbance at 242 nm.

Analysis showed that 40% of the cholesterol was converted to cholest-4-en-3-one after two hours of reaction time.

A control run under identical conditions but without the addition of cholesterol oxidase showed no detectable conversion of cholesterol to the more oxidized cholest-4-en-3-one.

EXAMPLE 4

In a stainless steel reactor of internal volume 150 ml were placed 80 mg disodium p-nitrophenyl phosphate and 1.0 ml deionized water. At a pressure of 1400 psi and a constant temperature of 35° C., carbon dioxide was pumped through this chamber at a flowrate of 400 ml per hour, dissolving some of the disodium p-nitrophenyl phosphate and some of the water. This solution was then passed through a packed bed of alkaline phosphatase immobilized on spherical glass beads. Dimensions of the packed bed reactor were 3×0.5 cm. The solution next passed through a 75 ml vessel kept at a temperature of 18° C. where products and any unreacted disodium p-nitrophenyl phosphate precipitated out of solution. The carbon dioxide was then recycled.

After three hours of operation, the pump was shut off and the system depressurized. The system was rinsed with 40 ml of deionized water and the water solution analyzed for p-nitrophenol by light absorptance at 410 nm. Typically, 30% conversion of disodium p-nitrophenyl phosphate was obtained after three hours of continuous operation.

I claim:

1. A method for producing a product or products by enzyme-catalyzed reaction, comprising the step of:
    contacting a substrate(s) and an enzyme(s) in the presence of a fluid under supercritical conditions of temperature and pressure of said fluid, whereby said substrate(s) is substantially soluble in said fluid under said conditions wherein said enzyme is selected from the group consisting of alkaline phosphatase and cholesterol oxidase and said enzyme is entrapped with water in reverse micelles.

2. A method according to claim 1 in which the supercritical fluid may contain a cosolvent to increase the solubility of reactant(s) or product(s) in the supercritical fluid.

3. A method according to claim 1 further comprising the step of removing a product(s) of said enzyme-catalyzed reaction from said fluid by changing the temperature, pressure, or both, of said fluid to effect precipitation of said product(s).

4. A method according to claim 1 wherein water is initially present in said fluid in an amount such that said enzyme-catalyzed reaction results in the production of water and a dehydration product derived from said substrate(s).

5. A method according to claims 1 or 2 wherein said fluid at supercritical conditions of temperature and pressure comprises carbon dioxide.

6. A method according to claims 1 or 2 wherein said fluid at supercritical conditions of temperature and pressure comprises a mixture of carbon dioxide, oxygen and cosolvent.

7. A method according to claim 1 wherein said enzyme is immobilized on a solid support.

8. A method according to claim 7 wherein said solid support comprises a packed bed of particles.

9. A method according to claim 7 wherein said solid support comprises a fluidized bed of particles.

* * * * *